United States Patent
Lehmann et al.

(10) Patent No.: US 7,319,095 B2
(45) Date of Patent: Jan. 15, 2008

(54) USE OF $GABA_B$ RECEPTOR AGONISTS

(75) Inventors: Anders Lehmann, Vastra Frolunda (SE); Sverker von Unge, Fjaras (SE)

(73) Assignee: AstraZeneca AB, Sodertalje (SE)

( * ) Notice: Subject to any disclaimer, the term of this patent is extended or adjusted under 35 U.S.C. 154(b) by 199 days.

(21) Appl. No.: 11/300,195

(22) Filed: Dec. 13, 2005

(65) Prior Publication Data

US 2006/0172979 A1 Aug. 3, 2006

Related U.S. Application Data

(63) Continuation-in-part of application No. 11/016,543, filed on Dec. 16, 2004, now Pat. No. 7,034,176, which is a continuation of application No. 10/406,838, filed on Apr. 4, 2003, now Pat. No. 6,841,698, which is a continuation of application No. 09/786,219, filed as application No. PCT/SE00/02426 on Dec. 4, 2000, now Pat. No. 6,576,626.

(60) Provisional application No. 60/639,458, filed on Dec. 27, 2004.

(30) Foreign Application Priority Data

Dec. 9, 1999 (SE) .................................. 9904508
Oct. 9, 2000 (SE) .................................. 0003640

(51) Int. Cl.
*A61K 31/66* (2006.01)
(52) U.S. Cl. ........................ 514/75; 514/114
(58) Field of Classification Search ................ None
See application file for complete search history.

(56) References Cited

U.S. PATENT DOCUMENTS

| | | | |
|---|---|---|---|
| 4,740,332 A | 4/1988 | Thottathil .................... 560/130 |
| 5,004,826 A | 4/1991 | Dingwall et al. ............ 558/166 |
| 5,036,057 A | 7/1991 | Martin ......................... 514/54 |
| 5,229,379 A | 7/1993 | Marescaux et al. ......... 514/114 |
| 5,281,747 A | 1/1994 | Hall et al. ................... 562/11 |
| 5,332,729 A | 7/1994 | Mickel et al. .............. 514/114 |
| 5,407,922 A | 4/1995 | Marescaux et al. ......... 514/114 |
| 5,461,040 A | 10/1995 | Hall et al. .................. 514/114 |
| 5,538,956 A | 7/1996 | Minchin et al. ............ 514/114 |
| 5,567,840 A | 10/1996 | Hall et al. .................. 562/11 |
| 6,117,908 A | 9/2000 | Andrews et al. ........... 514/114 |
| 6,576,626 B2 | 6/2003 | Elebring et al. ............ 514/114 |
| 6,596,711 B1 | 7/2003 | Amin et al. ................ 514/114 |
| 6,841,698 B2 | 1/2005 | Elebring et al. ............ 562/11 |
| 7,034,176 B2 | 4/2006 | Elebring et al. |
| 2005/0137414 A1 | 6/2005 | Elebring et al. ............ 558/190 |

FOREIGN PATENT DOCUMENTS

| | | |
|---|---|---|
| CH | 449046 | 4/1968 |
| EP | 0181833 | 5/1986 |
| EP | 0356128 | 2/1990 |
| EP | 0399949 | 11/1990 |
| EP | 0463969 | 1/1992 |
| EP | 506853 | 10/1992 |
| FR | 2722192 | 1/1996 |
| WO | 8704077 | 7/1987 |
| WO | 9611680 | 4/1996 |
| WO | 9811885 | 3/1998 |

OTHER PUBLICATIONS

U.S. Appl. No. 09/786,220, filed Mar. 1, 2001, Amin et al.
Froestl, et al. (1995), J. Med. Chem., 38, 3297-3312.
Zukin, et al. (1974), Proc. Natl. Acad. USA 71, 4802-4807.
Olpe et al. (1990), Eur. J. Pharmacol. 187, 27-38.
Holloway & Dent (1990), Gastroenterol. Clin. N. Amer. 19, 517-535.
The GABA Receptors; Second Edition, Edited by S.J. Enna and Norman Bowery, Humana Press (1997), pp. 281-282.
CA:123:2568411 Abs of Journal of Med Chem by Froestl et al., 38917, pp. 3297-3312 (1995).
CA:112:118949 Abs of Tetrahedron by Dingwall et al., 45(12), pp. 3787-3808 (1989).
Dingwall, J.G. et al., Diethoxymethylphosphonites and Phosphinates. Intermediates for the Synthesis of α, β- and γ-Aminoalkylphosphonous Acids, *Tetrahedron*, vol. 45, No. 12, pp. 3787-3808 (1989).
Hall, R..G., "Phosphinic Acid Analogues of γ-Aminobutyric acid (GABA). Synthesis of a New Radioligand", *Journal of Labelled Compounds and Radiopharmaceutics*, vol. 36, No. 2, pp. 129-135 (1995).

*Primary Examiner*—Sikarl A. Witherspoon
(74) *Attorney, Agent, or Firm*—White & Case LLP

(57) ABSTRACT

The present invention relates to the use of $GABA_B$ receptor agonists for the treatment as well as the prevention of cough.

7 Claims, No Drawings

USE OF GABA$_B$ RECEPTOR AGONISTS

This application is a continuation-in-part of U.S. patent application Ser. No. 11/016,543, filed Dec. 16, 2004 now U.S. Pat. No. 7,034,176, which is a continuation of U.S. patent application Ser. No. 10/406,838, filed Apr. 4, 2003, now U.S. Pat. No. 6,841,698, which is a continuation of U.S. patent application Ser. No. 09/786,219, filed Mar. 1, 2001, now U.S. Pat. No. 6,576,626, which is a §371 of international patent application PCT/SE00/02426, filed Dec. 4, 2000; and claims the benefit of U.S. Provisional Application No. 60/639,458, filed Dec. 27, 2004.

FIELD OF THE INVENTION

The present invention relates to the use of a GABA$_B$ receptor agonist for the treatment as well as the prevention of cough.

BACKGROUND OF THE INVENTION

GABA (4-aminobutanoic acid) is the main inhibitory neurotransmitter in the mammalian nervous system. GABA activates three major classes of receptors, namely GABA$_A$, GABA$_B$ and GABA$_C$, which have different characteristics. GABA$_B$ receptor agonists are known as useful in the treatment of CNS disorders, such as muscle relaxation in spinal spasticity, cardiovascular disorders, asthma, gut motility disorders such as irritable bowel syndrome (IBS) (WO 01/42252) and as prokinetic and anti-tussive agents (EP 0506853). GABA$_B$ receptor agonists have also been disclosed as being useful in the treatment of emesis (WO 96/11680) and in the inhibition of transient lower esophageal sphincter relaxation (WO 98/11885).

The most studied GABA$_B$ receptor agonist is baclofen (4-amino-3-(chlorophenyl)butanoic acid), known inter alia in the Swiss patent No. CH 449,046. Baclofen has for several years been used as an antispastic agent. EP 0319482 discloses (3-aminopropyl)methylphosphinic acid (3-APMPiA) while EP 0356128 describes the use of this specific compound, as a potent GABA$_B$ receptor agonist, in therapy. EP 0181833 discloses substituted 3-aminopropylphosphinic acids (3-APPiA), which have been found to have very high affinities towards GABA$_B$ receptor sites. In analogy to baclofen, these compounds can be used as for instance muscle relaxants. EP 0463969 and FR 2722192 are both related to 4-aminobutanoic acid derivatives having different heterocyclic substituents at the 3-carbon of the butyl chain. WO 01/42252 and WO 01/41743 disclose novel compounds, which have affinity to one or more GABA$_B$ receptors, and the use of these active compounds in therapy. EP 0506853 discloses the use of GABA$_B$ selective agonists for treating cough in mammals. Structure-activity relationships of several phosphinic acid analogues with respect to their affinities to the GABA$_B$ receptor as well as their muscle relaxant effect are discussed in J Med Chem. (1995), 38, 3297 3312.

There is still a need for a cough therapy which does not have the disadvantages of influencing the respiratory rate, and which has an acceptable bioavailability. The object of the present invention is therefore to find a novel therapy for treating cough.

OUTLINE OF THE INVENTION

Each of the following related applications for which this application makes and is entitled to a benefit claim is incorporated by reference in its entirety: U.S. patent application Ser. No. 11/016,543, filed Dec. 16, 2004, and which published as 20050137414 A1; U.S. patent application Ser. No. 10/406,838, filed Apr. 4, 2003, now U.S. Pat. No. 6,841,698; U.S. patent application Ser. No. 09/786,219, filed Mar. 1, 2001, now U.S. Pat. No. 6,576,626; international patent application PCT/SE00/02426, filed Dec. 4, 2000; and U.S. Provisional Application No. 60/639,458, filed Dec. 27, 2005.

The present invention is directed to the use of certain compounds, which are GABA$_B$-agonists, for the treatment as well as prevention of cough.

Consequently, one aspect of the present invention is therefore directed to the use of a compound of formula (I)

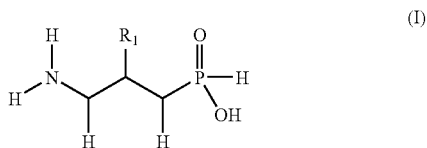

(I)

wherein R$_1$ represents a hydroxy group, a halogen or an oxo group; as well as a pharmaceutically acceptable salt, a solvate or an optical isomer thereof, for the manufacture of a medicament for the treatment of cough. One embodiment of the present invention relates to the use of said compound of formula (I) for the manufacture of a medicament for the treatment of cough, wherein R$_1$ is fluorine.

Examples of compounds of formula (I), useful in accordance with the present invention are (3-amino-2-fluoropropyl)phosphinic acid; (2R)-(3-amino-2-fluoropropyl)phosphinic acid; (2S)-(3-amino-2-fluoropropyl)phosphinic acid; (3-amino-2-fluoro-1-methylpropyl)phosphinic acid; (3-amino-2-oxopropyl)phosphinic acid; (2S)-(3-amino-2-hydroxypropyl)phosphinic acid; (R)-(3-amino-2-hydroxypropyl)phosphinic acid; and (3-amino-1-fluoro-2-hydroxypropyl)phosphinic acid.

A further aspect of the present invention is directed to the use of a compound of formula (II)

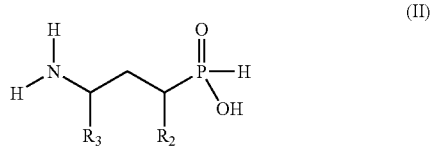

(II)

wherein R$_2$ represents hydrogen, a hydroxy group, C$_1$-C$_7$ alkyl, C$_1$-C$_7$ alkoxy or halogen; R$_3$ represents hydrogen, C$_1$-C$_7$ alkyl (optionally substituted with hydroxy, mercapto, C$_1$-C$_7$ alkoxy, C$_1$-C$_7$ thioalkoxy, aryl or heteroaryl), aryl or heteroaryl; with the proviso that R$_2$ and R$_3$ are not hydrogen at the same time; as well as a pharmaceutically acceptable salt, a solvate or an optical isomer thereof, for manufacture of a medicament for the treatment of cough.

In yet another aspect, the present invention is directed to the use of a compound of formula (III)

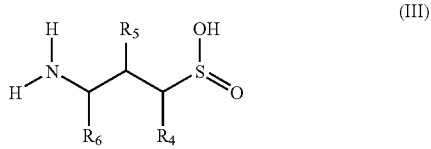

wherein $R_4$ represents hydrogen, a hydroxy group or halogen;

$R_5$ represents hydrogen, a hydroxy group, mercapto, halogen, or an oxo group;

$R_6$ represents hydrogen or $C_1$-$C_7$ alkyl (optionally substituted with hydroxy, mercapto, $C_1$-$C_7$ alkoxy, $C_1$-$C_7$ thioalkoxy, aryl or heteroaryl), aryl or heteroaryl; as well as a pharmaceutically acceptable salt, a solvate or an optical isomer thereof, for the manufacture of a medicament for the treatment of cough.

Examples of compounds of formula (III) useful in accordance with the present invention are (3-amino-2-fluoropropyl)sulphinic acid, (2S)-(3-amino-2-fluoropropyl)sulphinic acid, (2R)-(3-amino-2-fluoropropyl)sulphinic acid, (2S)-(3-amino-2-hydroxypropyl)sulphinic acid, (2R)-(3-amino-2-hydroxypropyl)sulphinic acid and (3-amino-2-oxopropyl)sulphinic acid.

A further aspect of the present invention is the use of any compound of formula (I), (II) and (III) as defined above for the prevention of cough. The term "prevention" referred to herein includes the inhibition of cough. Moreover, the "prevention" effect of the present invention provides for an inhibition of the cough reflex.

Yet a further aspect of the present invention relates to a method for the treatment of cough, comprising administering to a subject, in need of such treatment, a pharmaceutically and pharmacologically effective amount of a compound of formula (I), (II) and (III) as defined above. According to one embodiment of the present invention said treatment is prevention of cough. According to yet another embodiment of the present invention said cough is chronic cough.

Cough is an expulsive reflex initiated when foreign bodies like infection, noxious fumes or dust irritate the respiratory tract, i.e. the throat, larynx and airway. This results in a sudden expulsion of air, which will clear the breathing passages from the substances causing the irritation. The cough reflex as such is quite complex and as yet not completely understood. A variety of peripheral sites are connected to the cough centre in the medulla, including the nose, auditory canal, nasopharynx, larynx, trachea, intrapulmonary bronchi and pleural surfaces and simulation of the receptors in these site can also result in cough.

There are different kinds of coughs; some coughs are non-productive, also called dry, while others are productive (phlegm is brought up). A cough can also be either acute or chronic. A cough can also be spontaneous and voluntary. A subject suffering from cough will often experience said cough as irritating and the coughing will often have an impact on the quality of life due to e.g. sleeping problems, thus decreasing the productivity of a subject. The present invention is thus directed to improvement of the life quality for subject suffering from cough.

Cough, especially chronic cough, is caused by one or more of the following factors including: allergies and asthma, chronic obstructive pulmonary disease also called COPD (e.g. chronic bronchitis), upper respiratory tract infections, also called URTI (can cause a transient airway hyperresponsiveness), sinusitis leading to postnasal drip, acute viral infection, cancer (bronchogenic or esophageal), interstitial lung disease (e.g. emphysema or sarcoidosis), gastroesophageal reflux disease (GERD), bronchiectasis, chronic lung infections (e.g. tuberculosis), recurrent aspiration, pressure from an intrathoracic mass (e.g. thoracic aneurysm), irritation of cough receptors in the ear, lymphangitis carciomatosis, reactive airways dysfunction syndrome, vocal cord dysfunction, plentitis, psychogenic, angiotensin converting enzyme-induced cough, medical-related (ACE-inhibitors and beta blockers), congestive heart failure and smoking, and other environmental irritants.

The wording cough as used throughout the present specification and claims, includes chronic cough, acute cough as well as non-productive-cough, productive cough, spontaneous cough and voluntary cough. The term chronic cough is defined in accordance with Kardos P et al (The German Respiratory Society's Guideline for the Diagnosis and Treatment of Patients with Acute and Chronic Cough Medizinische Klinik 2004;99(8):468-75) as a cough that lasts longer than 8 weeks. However, chronic cough can also be defined as a cough lasting longer than 3 weeks or as a cough lasting longer than 2 months. The term "acute cough" is also defined in accordance with the reference above as a cough lasting less than 8 weeks.

The term "halogen" means fluorine, chlorine, bromine or iodine.

In the definition of formula (1), it is to be understood that when $R_1$ is an oxo group the bond between $R_1$ and the carbon is a double bond, i.e. a carboxy group. Within the scope if the present invention, it is also to be understood that when $R_5$ is an oxo group the bond between $R_5$ and the carbon is a double bond, i.e. a carboxy group.

The term "$C_1$-$C_7$ alkyl" includes straight, branched or cyclic alkyl, for example, $C_1$-$C_4$ alkyl, such as methyl, ethyl, n-propyl or n-butyl, and also isopropyl, isobutyl, secondary butyl or tertiary butyl, but may also be a $C_5$-$C_7$ alkyl group such as a pentyl, hexyl or heptyl group.

In this specification is the term "$C_1$-$C_7$ alkoxy" to be understood as to include for example, $C_1$-$C_4$ alkoxy, such as methoxy, ethoxy, n-propoxy or n-butoxy, and also isopropoxy, isobutoxy, secondary butoxy or tertiary butoxy, but may also be a $C_5$-$C_7$ alkoxy group, such as a pentoxy, hexoxy or heptoxy group.

The term "$C_1$-$C_7$ thioalkoxy" is, for example, $C_1$-$C_4$ thioalkoxy, such as thiomethoxy, thioethoxy, n-thiopropoxy or n-thiobutoxy, and also thioisopropoxy, thioisobutoxy, secondary thiobutoxy or tertiary thiobutoxy, but may also be a $C_5$-$C_7$ thioalkoxy group, such as a thiopentoxy, thiohexoxy or thioheptoxy group.

The herein used term "aryl" means aromatic rings having from 6-14 carbon atoms including both monocyclic rings and polycyclic ring systems, such as phenyl or naphtyl, optionally substituted with one or more substituents such as $C_1$-$C_7$ alkyl, $C_1$-$C_7$ alkoxy, $C_1$-$C_7$ thioalkoxy, halogen, hydroxy, mercapto, carboxylic acid, carboxylic acid ester, carboxylic acid amide or nitrile.

The term "heteroaryl" as used herein includes heteroaromatic rings having from 5-14 atoms, including both monocyclic rings and polycyclic ring systems, in which one or several of the ring atoms is oxygen, nitrogen or sulphur. The heteroaryl is optionally substituted with one or more substituents such as $C_1$-$C_7$ alkyl, $C_1$-$C_7$ alkoxy, $C_1$-$C_7$ thioalkoxy, halogen, hydroxy, mercapto, carboxylic acid, carboxylic acid ester, carboxylic acid amide or nitrile.

The compounds according to formula (I), formula (II) and formula (III) are of amphoteric nature and may be presented in the form of internal salts. They can also form acid addition salts and salts with bases. Such salts are particularly pharmaceutically acceptable acid addition salts, as well as pharmaceutically acceptable salts formed with bases. Suitable acids for the formation of such salts include, for example, mineral acids such as hydrochloric, hydrobromic, sulfuric, or phosphoric acid or organic acids such as sulfonic acids and carboxylic acids. Salts with bases are, for example, alkali metal salts, e.g. sodium or potassium salts, or alkaline earth metal salts, e.g. calcium or magnesium salts, as well as ammonium salts, such as those with ammonia or organic amines.

Some of the compounds of formula (I), formula (II) and formula (III) may have chiral centers and/or geometric isomeric centers (E- and Z-isomers), and it is to be understood that the invention encompasses all such optical, diastereoisomers and geometric isomers. When one or more stereocentre is present in the molecule, the compounds according to formula (I), formula (II) and formula (III) can be in the form of a stereoisomeric mixture, i.e. a mixture of diastereomers and/or racemates, or in the form of the single stereoisomers, i.e. the single enantiomer and/or diastereomer. The compounds can also be in the form of solvates, e.g. hydrates. The use of any such salt, isomer or any other form of the compound of formula (I), (II) and (III) for the treatment as well as the prevention of cough, is within the scope of the present invention.

The compounds of formula (I), formula (II) and formula (III) or salts, solvates or stereoisomers are known from e.g. WO 01/42252 and WO 01/41743, which documents also disclose methods for their preparation.

In literature the phosphinic acids having a hydrogen atom attached to phosphorous are also named phosphonous acids. However, these are two names for the same compounds and both names can be used.

Pharmaceutical Formulations

For clinical use, the compounds are in accordance with the present invention suitably formulated into pharmaceutical formulations for oral administration. Also rectal, parenteral or any other suitable route of administration may be contemplated to the skilled man in the art of formulations. Thus, the compounds are formulated with at least one pharmaceutically and pharmacologically acceptable carrier or adjuvant. The carrier may be in the form of a solid, semi-solid or liquid diluent.

In the preparation of oral pharmaceutical formulations in accordance with the invention, the compound(s) to be formulated is mixed with solid, powdered ingredients such as lactose, saccharose, sorbitol, mannitol, starch, amylopectin, cellulose derivatives, gelatin, or another suitable ingredient, as well as with disintegrating agents and lubricating agents such as magnesium stearate, calcium stearate, sodium stearyl fumarate and polyethylene glycol waxes. The mixture is then processed into granules or compressed into tablets.

Soft gelatine capsules may be prepared with capsules containing a mixture of the active compound or compounds of the invention, vegetable oil, fat, or other suitable vehicle for soft gelatine capsules. Hard gelatine capsules may contain the active compound in combination with solid powdered ingredients such as lactose, saccharose, sorbitol, mannitol, potato starch, corn starch, amylopectin, cellulose derivatives or gelatine.

Dosage units for rectal administration may be prepared (i) in the form of suppositories which contain the active substance(s) mixed with a neutral fat base; (ii) in the form of a gelatine rectal capsule which contains the active substance in a mixture with a vegetable oil, paraffin oil, or other suitable vehicle for gelatine rectal capsules; (iii) in the form of a ready-made micro enema; or (iv) in the form of a dry micro enema formulation to be reconstituted in a suitable solvent just prior to administration.

Liquid preparations for oral administration may be prepared in the form of syrups or suspensions, e.g. solutions or suspensions, containing the active compound and the remainder of the formulation consisting of sugar or sugar alcohols, and a mixture of ethanol, water, glycerol, propylene glycol and polyethylene glycol. If desired, such liquid preparations may contain colouring agents, flavouring agents, saccharine and carboxymethyl cellulose or other thickening agent. Liquid preparations for oral administration may also be prepared in the form of a dry powder to be reconstituted with a suitable solvent prior to use.

Solutions for parenteral administration may be prepared as a solution of a compound of the invention in a pharmaceutically acceptable solvent. These solutions may also contain stabilizing ingredients and/or buffering ingredients and are dispensed into unit doses in the form of ampoules or vials. Solutions for parenteral administration may also be prepared as a dry preparation to be reconstituted with a suitable solvent extemporaneously before use.

In one aspect of the present invention, the $GABA_B$ receptor agonist may be administered once or twice daily, depending on the severity of the patient's condition. A typical daily dose of the $GABA_B$ receptor agonist is 0.1-100 kg body weight of the subject to be treated, but this will depend on various factors such as the route of administration, the age and weight of the patient as well as of severity of the patient's condition.

The compounds according to the present invention may also be administered by inhalation orally or intranasally. They can also be adapted to be administered from a dry powder inhaler, a pressurised metered dose inhaler or a nebuliser. When said compounds are administered from a pressurised inhaler they are either suspended or dissolved in a liquid propellant mixture. When said compounds are administered via a nebuliser they may be in the form of a nebulised suspension or a solution with or without a suitable pH or tonicity adjuster, either as a unit dose or a multidose device.

It has surprisingly been found that certain $GABA_B$ receptor agonist compounds can be used for treating and/or preventing cough without affecting the respiratory rate of a subject. Furthermore, these compounds have also the important characteristics of excellent bioavailability, excellent half-life and that they can be in a form suitable for oral administration.

The $GABA_B$ compounds according to the present invention can also be combined with different types of active compounds for instance proton pump inhibitors, ACE-inhibitors, beta-2 agonsits or beta-blockers in order to manufacture a medicament for the treatment as well as the prevention of cough.

Biological Evaluation

The present invention will be further described below by way of examples. However, these examples are not to be construed in any way as limiting to the invention.

I. Evaluation of the Ability of $GABA_B$ Receptor Agonist to Prevent Cough and Reflex Bronchospasm via Central and Peripheral Actions.

Experimental Design

Citric acid-induced cough was evoked in conscious guinea pigs. Male Hartley guinea pigs (300-400 g) were placed in a chamber with a continuous flow of air. Positive and negative pressure changes within the chamber were used to monitor the expiratory and inspiratory phases of respiration. A nebuliser was connected in series with the air pump, allowing aerosol delivery of citric acid (0.1-1 M).

Cough was defined based on the visual appearance of the respiratory manoeuvre, the characteristic sound, and by a signature pressure trace typified by an expiratory effort that produced a positive chamber pressure 10-20 times higher than that associated with tidal breathing and proceeded by a rapid and pronounced inspiratory effort. All data were recorded digitally. The total number of coughs and the estimated concentration of citric acid evoking 1, 2 and 5 coughs were determined for each experiment.

Four treatment groups were employed in this study: Vehicle control, baclofen, (2R)-(3-amino-2-fluoropropyl) phosphinic acid and (3-aminopropyl)phosphinic acid (3-AP-PiA). The $GABA_B$ receptor agonists were administered subcutaneously, 30 minutes prior to initiating the cough challenge, at a dose of 1 mg/kg. $GABA_B$ receptor agonists that exhibited antitussive effects at a dose of 1 mg/kg were studied at several additional doses (0.1-10 mg/kg) to determine relative potencies. Agonists that exhibited little if any antitussive activity at a dose of 1 mg/kg were studied at 10 and 30 mg/kg in an attempt to uncover antitussive effects. To assess CNS depressant effects of these compounds, their effects on respiratory rate and respiratory pattern (inspiratory and expiratory times) were assessed and compared to control.

Results

A. Inhibition of cough induced by citric acid in conscious guinea pigs by subcutaneously administered $GABA_B$ agonists

TABLE 1

Cumulative number of coughs evoked by citric acid: Effects of Vehicle, Baclofen and (3-aminopropyl)methyl phosphinic acid (SKF97541)

| Citric Acid [M] | Control (n = 15) | 0.3 mg/kg Baclofen (n = 3) | 3 mg/kg Baclofen (n = 6) | 0.3 mg/kg SKF97541 (n = 5) |
| --- | --- | --- | --- | --- |
| 0 | 0 ± 0 | 0 ± 0 | 0 ± 0 | 0 ± 0 |
| 0.01 | 0.5 ± 0.3 | 1.0 ± 0 | 0 ± 0 | 0 ± 0 |
| 0.1 | 3.0 ± 0.9 | 3.0 ± 0.6 | 1.0 ± 0.5 | 0.4 ± 0.2 |
| 0.3 | 12.9 ± 2.7 | 12.3 ± 7.4 | 6.0 ± 1.9 | 3.8 ± 1.6 |
| 1 | 27.2 ± 3.3 | 25.7 ± 4.8 | 14.3 ± 3.8 | 19.2 ± 5.8 | n = the number of guinea pigs

TABLE 2

Cumulative number of coughs evoked by citric acid: Effect of (2R)-(3-amino-2-fluoropropyl) phosphinic acid.

| Citric Acid [M] | Control (n = 15) | 0.3 mg/kg (n = 5) | 3 mg/kg (n = 8) | 10 mg/kg (n = 8) |
| --- | --- | --- | --- | --- |
| 0 | 0 ± 0 | 0 ± 0 | 0 ± 0 | 0 ± 0 |
| 0.01 | 0.5 ± 0.3 | 0 ± 0 | 0.1 ± 0.1 | 0 ± 0 |
| 0.1 | 3.0 ± 0.9 | 3.4 ± 1.1 | 1.9 ± 1.1 | 0.6 ± 0.3 |
| 0.3 | 12.9 ± 2.7 | 11.4 ± 1.3 | 9.0 ± 3.8 | 3.8 ± 1.3 |
| 1 | 27.2 ± 3.3 | 27.6 ± 3.7 | 15.4 ± 3.6 | 9.7 ± 1.9 | n = the number of guinea pigs

TABLE 3

Cumulative number of coughs evoked by citric acid: Effect of 3-APPiA

| Citric Acid [M] | Control (n = 15) | 0.3 mg/kg (n = 4) | 3 mg/kg (n = 7) |
| --- | --- | --- | --- |
| 0 | 0 ± 0 | 0 ± 0 | 0 ± 0 |
| 0.01 | 0.5 ± 0.3 | 0 ± 0 | 0 ± 0 |
| 0.1 | 3.0 ± 0.9 | 0.2 ± 0.2 | 1.7 ± 0.9 |
| 0.3 | 12.9 ± 2.7 | 7.8 ± 3.0 | 3.9 ± 1.6 |
| 1 | 27.2 ± 3.3 | 28.8 ± 2.9 | 16.1 ± 5.2 | n = the number of guinea pigs

B. Effects of subcutaneously administered $GABA_B$ agonists on baseline respiratory rate in conscious guinea pigs

TABLE 4

Result of study B

| | mean |
| --- | --- |
| Baclofen | |
| 0.3 mg/kg | 96.8 ± 8.5 |
| 3 mg/kg | 78.1 ± 17.6 |
| (3-aminopropyl)methyl phosphinic acid | |
| 0.1 mg/kg | 79.2 ± 16.5 |
| 0.3 mg/kg | 68.6 ± 6.0 |
| (2R)-(3-amino-2-fluoropropyl phosphinic acid | |
| 0.3 mg/kg | 99.2 ± 2.7 |
| 3 mg/kg | 94.7 ± 5.0 |
| 10 mg/kg | 97.2 ± 3.4 |
| 3-APPiA | |
| 0.3 mg/kg | 93.0 ± 5.6 |
| 3 mg/kg | 97.9 ± 4.2 |
| Placebo | 96.2 ± 3.8 |

II. Evaluation of the Pharmacokinetic Properties

In the present studies dogs received single intravenous and oral doses of 3-APPiA, (2R)-(3-amino-2-fluoropropyl) phosphinic acid (A), (2S)-(3-amino-2-hydroxypropyl)phosphinic acid (B), (3-amino-2-oxopropyl)phosphinic acid (C) and 3-amino-2-fluoropropyl)phosphinic acid (D) at therapeutic doses. The plasma concentrations of each compound was determined by LC-MS. The mean values of the total plasma clearance (CL), the half-life ($T_{1/2}$), the volume of distribution at steady state ($V_{ss}$), the oral availability (F), are summarised in Table 5.

Experimental Design

Eight female Beagle and four Labrador dogs were used. The dogs were identified by a number tattooed in the ear.

The animals had free access to water and were fed once a day (GLP diet) at approximately 1 p.m. On the experimental day, the dogs had not eaten since approximately 1 p.m. on the day before and were not allowed to eat until 6 hours after dosing.

The test formulations were administered intravenously in a superficial front leg vein (this vein was not used for blood sampling during 2 hours after dosing) or orally by gavage. The gavage tube was rinsed with about 20 mL of water and emptied with 20 mL of air before it was taken out. The oral and intravenous dose volumes were 1 and 0.5 mL/kg, respectively.

Blood samples of about 2 mL were taken from a superficial front leg vein pre-dose and at 5, 10, 20, 40, 90 minutes, 3, 5, 8 and 24 hours after dosing. The blood samples were collected in heparinized glass tubes (Venoject®) and centrifuged (10 min, 3000 g, +4° C.). The plasma was then transferred to plastic tubes and stored at about −20° C. until analysis.

The pharmacokinetic parameters were calculated by non-compartment analysis using WinNonlin Professional (Pharsight Corporation, California, USA). The area under the plasma concentration-time curve ($AUC_{(0,t)}$) was calculated using a combination of the linear and logarithmic trapezoidal rule from the time of administration to the sampling time with the last determinable plasma concentration (3, 5, 8 or 24 h). For the intravenous bolus dose, the concentration at time zero ($C_{(0)}$) was estimated by log-linear regression of the first two concentration-time points. The $AUC_{(0-t)}$ was extrapolated to infinity by adding $C_t/k$. $C_t$ was the predicted plasma concentration at the time of the last plasma sample with a determinable concentration and k was the apparent terminal rate constant. $C_t$ and k were obtained by linear least-squares regression analysis of the logarithm of the last 3 to 5 plasma concentrations versus time. The apparent terminal half-life ($t_{1/2}$) was calculated as $\ln 2/k$, wherein k is elimination constant, i.e. the slope of the decreasing curve.

The oral bioavailability (F) for each dog was calculated from individual AUC (area under the curve) and dose values. The calculation was made as follows: $(AUC_{po} \cdot Dose_{iv} / AUC_{iv} \cdot Dose_{po}) \cdot 100$.

Estimates of total plasma clearance and of volume of distribution were calculated from plasma concentration data obtained after intravenous bolus injection. The total plasma clearance (CL) was calculated as $Dose_{i.v.}/AUC_{i.v.}$, and the volume of distribution at steady state ($V_{ss}$) was calculated as $MRT_{i.v.} \cdot CL$. The mean residence time after intravenous administration ($MRT_{i.v.}$) was calculated as AUMC/AUC for bolus injection, wherein AUMC is the area under the first-moment versus time curve. The results are presented by descriptive statistics. The pharmacokinetic parameters are presented as geometric mean and range.

TABLE 5

Summary of pharmacokinetic parameters in female dogs following intravenous and oral dosing, geometric mean (range)

| Compound | Dose (μmol/kg) | n | CL (mL/min/kg) | $T_{1/2}$ (h) | $V_{ss}$ (L/kg) | F (%) |
|---|---|---|---|---|---|---|
| 3-APPiA | 2 | 2 | 20 (16-25) | 0.52 (0.51-0.54) | 0.55 (0.34-0.88) | 10 (8.5-12) |
| A | 7 | 4 | 2.1 (0.37-3.4) | 7.5 (6.8-8.7) | 1.1 (0.84-1.4) | 88 (80-97) |
| B | 3 | 2 | 6.67 (5.9-7.5) | 0.50 (0.37-0.68) | 0.25 (0.22-0.28) | 86 (82-90) |
| C | 3 | 2 | 8.2 (6.5-10) | 2.5 (2.5-2.6) | 0.74 (0.55-0.98) | 60 (55-65) |
| D | 7 | 2 | 5.2 (4.0-6.7) | 8.2 (4.5-15) | 2.3 (1.5-3.3) | 54 (31-92) |

The invention claimed is:

1. A method for inhibiting or treating cough, comprising administering to a subject in need thereof a pharmaceutically and pharmacologically effective amount of a compound of formula (I)

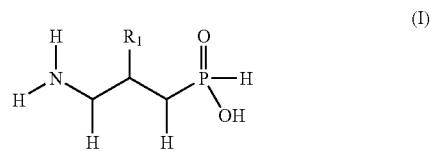

(I)

as well as a pharmaceutically acceptable salt, a solvate or an optical isomer thereof, wherein
$R_1$ represents a hydroxy group, a halogen or an oxo group.

2. The method according to claim 1, wherein said halogen is fluorine.

3. The method according to claim 1, wherein the cough is chronic cough.

4. A method for inhibiting or treating cough, comprising administering to a subject in need thereof a pharmaceutically and pharmacologically effective amount of a compound of formula (II)

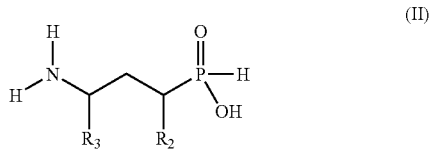

(II)

as well as a pharmaceutically acceptable salt, a solvate or an optical isomer thereof, wherein
$R_2$ represents hydrogen, a hydroxy group, $C_1$-$C_7$ alkyl, $C_1$-$C_7$ alkoxy or halogen;
$R_3$ represents hydrogen, $C_1$-$C_7$ alkyl (optionally substituted with hydroxy, mercapto, $C_1$-$C_7$ alkoxy, $C_1$-$C_7$ thioalkoxy, aryl or heteroaryl), aryl or heteroaryl;
with the proviso that $R_2$ and $R_3$ are not hydrogen at the same time.

5. The method according to claim 4, wherein the cough is chronic cough.

6. A method for inhibiting or treating cough, comprising administering to a subject in need thereof a pharmaceutically and pharmacologically effective amount of a compound of formula (III)

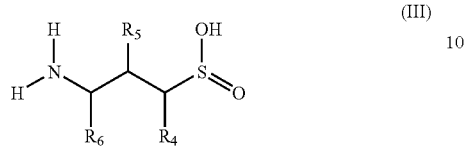

as well as a pharmaceutically acceptable salt, a solvate or an optical isomer thereof, wherein $R_4$ represents hydrogen, hydroxy group or halogen;

$R_5$ represents hydrogen, hydroxy group, mercapto, halogen, or an oxo group;

$R_6$ represents hydrogen or $C_1$-$C_7$ alkyl (optionally substituted with hydroxy, mercapto, $C_1$-$C_7$ alkoxy, $C_1$-$C_7$ thioalkoxy, aryl or heteroaryl), aryl or heteroaryl.

7. The method according to claim 6, wherein the cough is chronic chough.

* * * * *